(12) United States Patent
Nieuwenhuijsen

(10) Patent No.: US 8,652,545 B2
(45) Date of Patent: Feb. 18, 2014

(54) COMPOSITION OF A LIQUID DIETARY SUPPLEMENT TO TREAT SYMPTOMS OF AUTISM SPECTRUM DISORDERS IN CHILDREN

(75) Inventor: Bart Nieuwenhuijsen, Philadelphia, PA (US)

(73) Assignee: Reverta Health Solutions LLC, Penn Valley, PA (US)

( * ) Notice: Subject to any disclaimer, the term of this patent is extended or adjusted under 35 U.S.C. 154(b) by 802 days.

(21) Appl. No.: 12/370,577

(22) Filed: Feb. 12, 2009

(65) Prior Publication Data

US 2009/0202445 A1    Aug. 13, 2009

Related U.S. Application Data

(60) Provisional application No. 61/028,328, filed on Feb. 13, 2008.

(51) Int. Cl.
 *A61K 36/28* (2006.01)
 *A61K 36/00* (2006.01)

(52) U.S. Cl.
 USPC ............................. 424/764; 424/725; 424/778

(58) Field of Classification Search
 None
 See application file for complete search history.

(56) References Cited

U.S. PATENT DOCUMENTS

| 6,271,259 | B1 | 8/2001 | Kakuda |
| 6,399,114 | B2 | 6/2002 | Foreman |
| 6,632,461 | B1 | 10/2003 | Slimak |
| 6,811,769 | B2 | 11/2004 | Watanabe |
| 7,419,693 | B2 | 9/2008 | Kester et al. |
| 7,534,450 | B2 | 5/2009 | Walsh et al. |

OTHER PUBLICATIONS

Barker et al. Retrieved from the internet. <http://web.archive.org/web/20050312091520/http://www.townsendletter.com/Oct2004/natperspect1004.htm>. Web archive date Mar. 12, 2005. Retrieved on Oct. 28, 2010. pp. 1-9.*
About Herbology. Retrieved from the internet. <http://web.archive.org/web/20000124113842/http://viable-herbal.com/herbology1/herbs42.htm>. Web archive date Jan. 24, 2000. Retrieved on Oct. 28, 2010. pp. 1-4.*
Eason. The Modern Day Druidess. Citadel Press. 2004. p. 132.*
Cardinali et al. Sleep and Sleep Disorders: A Neuropsychopharmacological Approach. Birkhauser. 2006. p. 300.*
Lake. Textbook of Integrative Mental Health Care. Thieme. 2006. p. 206.*
Georgarakis et al. Trace Elements in Gum Mastic of Chios. Chimika Chronika. 1992. 21 (1-24). Abstract.*
Magnesium in biology. Wikipedia.org. <http://en.wikipedia.org/wiki/Magnesium_in_biology>. Retrieved from the internet. Retrieved on Mar. 29, 2011. 17 pages.*
Liquid-liquid extraction. Wikipedia.org. <http://en.wikipedia.org/wiki/Liquid-liquid_extraction>. Retrieved from the internet. Retrieved on Mar. 30, 2011. 7 pages.*
In vitro and in vivo antimicrobial effects of mastic chewing gum against *Streptococcus mutans* and mutans streptococci Alev Aksoy et al., Archives of Oral Biology (2006) 51, 476-481.
B6-responsive disorders: A model of vitamin dependency, Peter T. Clayton, J Inherit Metab Dis (2006) 29:317-326.
Mastic Gum Kills *Helicobacter pylori*, Farhad U. Huwez, M.R.C.P., Ph.D, et al., New England Journal of Medicine, Dec. 24, 1998, vol. 339, No. 26, pp. 1946.
Dysregulated Innate Immune Responses in Young Children with Autism Spectrum Disorders: Their Relationship to Gastrointestinal Symptoms and Dietary Intervention, Harumi Jyonouchi, et al. Neuropsychobiology 2005;51:77-85 : Published online Feb. 28, 2005.
Combined vitamin B6-magnesium treatment in autism spectrum disorder (Review), Nye C, Brice A., The Cochrane Collaboration and published in The Cochrane Library 2009, Issue 1, 20 pages.
Differences between the gut microflora of children with autistic spectrum disorders and that of healthy children, Helena M. R. T. Parracho, et. al., Journal of Medical Microbiology (2005), 54, 987-991.
Intestinal Pathophysiology in Autism, John F. White, 1535-3702/03/2286-0639 Copyright © 2003 by the Society for Experimental Biology and Medicine, Intestinal Pathophysiology in Autism, pp. 639 to 649.
NIH—dietary supplement fact sheet, Magnesium, 9 pages, http://ods.od.nih.gov/pdf/factsheets/magnesium.pdf) retrieved Jan. 27, 2011.
F. Kottakis et al.; Arabino-Galactan Proteins from *Pistacia lentiscus* var. *chai*: isolation, . . . ; Amino Acids (2008); May 21, 2007; pp, 413-420; The Netherlands.
Unknown author; Mastic; The New England Journal of Medicine (ISSN 0028-4793); Dec. 24, 1998; vol. 339; 1946; U.S.; definition of the word "mastic".
Sotirios Paraschos et al.; In Vitro and In Vivo Activities of Chios Mastic Gum Extracts . . . ; Feb. 2007; pp. 551-559; vol. 51, No. 2; Antimicrobal Agents and Chemotherapy.
Albert H.C. Wong, MD, et al; Herbal Remedies in Psychiatric Practice; Arch Gen Psychiatry; pp. 1033-1040; 1998; vol. 55, Nov. 1998; www.archgenpsychiatry.com.
E.M. Williamson; Synergy and other interactions in phytomedicines; Phytomedicine; pp. 401-409; vol. 8(5); Urban & Fischer Verlag 2001.

* cited by examiner

*Primary Examiner* — Chris R Tate
(74) *Attorney, Agent, or Firm* — Stephen G Stanton

(57) ABSTRACT

The object of the present invention is to provide an all-natural dietary supplement formulation that may be beneficial to the management of behavioral and neurological symptoms associated with autism spectrum disorders; symptoms that may not be effectively improved by conventional drug treatment and behavioral therapy alone.

12 Claims, No Drawings

COMPOSITION OF A LIQUID DIETARY SUPPLEMENT TO TREAT SYMPTOMS OF AUTISM SPECTRUM DISORDERS IN CHILDREN

The present invention claims priority to U.S. provisional application 61/028,328 filed Feb. 13, 2008. This invention relates to a composition of a liquid dietary supplement to treat symptoms often displayed by children who have been diagnosed with an autism spectrum disorder.

SUMMARY

The product is comprised of the water-soluble extract of mastic gum, theanine, Passionflower extract, Feverfew extract and vitamin B6.

The present invention aims to improve the behavioral and neurological symptoms of autism spectrum disorders by targeting the areas that are most commonly affected in children with autism spectrum disorders, such as: social behavior, intestinal functioning, sleep, anxiety and brain neuropathy.

The present invention is a dietary supplement in the form of a syrup that is given to the child once to twice a day at a dose of about 1 to about 3 teaspoon(s) (about 5 to about 15 ml), based on the child's age. The syrup can be mixed with a beverage if needed. The same objective may be reached with a chewable tablet, capsule, gel cap, lollipop, lozenge, powder or effervescent tablet that contains the same formulation as the liquid formulation.

DESCRIPTION

The present invention relates to a composition of a liquid dietary supplement to treat symptoms of autism spectrum disorders in children.

The product is comprised of the following components:
(1) Mastic Gum: The present formulation contains the water-soluble extract of mastic gum at a final concentration of about 5 to about 100 mg/ml. Based on scientific studies, mastic gum, a resin from the mastic tree (*Pistacia lentiscus*) found primarily on the Greek island of Chios, can effectively eradicate the bacterium *H. pylori* in the gut (Huwez et al., 1998) and acts as an anti-inflammatory substance (Aksoy et al., 2006).
(2) Theanine: The present formulation contains theanine at a concentration of about 1 to about 10 mg/ml. Theanine, an amino acid commonly found in tea, easily crosses the blood-brain barrier. It has been found to reduce stress and to promote a more restful deep sleep.
(3) Passionflower extract: The present formulation contains Passionflower extract at a concentration of about 5 microgram/ml to about 100 microgram/ml. Passionflower extract has a long history of use among Native Americans in North America. It is commonly used to treat insomnia, hysteria and epilepsy and may also be effective for anxiety.
(4) Feverfew extract: The present formulation contains Feverfew extract at a concentration of about 5 microgram/ml to about 100 microgram/ml. Feverfew is a medicinal extract that is often used to treat migraines and digestive problems.
(5) Vitamin B6: The present formulation contains Vitamin B6 at a concentration of about 200 microgram/ml to about 10 mg/ml. Vitamin B6 is a water-soluble compound that can exists as three forms in the body. All three forms of vitamin B6 are precursors of an activated compound known as pyridoxal 5'-phosphate (PLP), which plays a vital role as the cofactor of a large number of essential enzymes in the human body.

The present invention aims to alleviate or reverse the various symptoms of autism by targeting the various areas that are affected in autism spectrum disorders:
(1) Improved gut functioning:
It has long been suggested that improper bowel function and inflammation in the gut are partly responsible for the behavioral symptoms of autism (White 2003, Parracho et al., 2005, Jyonouchi et al., 2005). Many neuropeptides are synthesized in the gut and are important for proper brain functioning.
The synthesis and/or the absorption of these neuropeptides in the gut may be compromised by inflammatory processes in the intestines of individuals with autism.
Mastic Gum and Feverfew extracts are included in the present formulation to aid in the proper functioning of the intestines, thereby improving normal brain function. The present inventor has found that a formulation including mastic gum improves social behavior in children with autism.
(2) Improved sleep patterns:
Since many children with autism spectrum disorders have disturbed sleep patterns, the present inventor included theanine and passionflower extracts in the formulation.
The reasoning behind this is that a well-rested child will function better in daily life.
(3) Decreased anxiety:
Many children with autism show increased levels of anxiety combined with high frustration levels, both of which interfere with social behavior.
The Passionflower extract in the present formulation aims to decrease anxiety.
(4) Brain Neuropathy
Vitamin B6 deficiency is believed to result in the development of neuropathy (For review, see Clayton (2006)).
Studies have shown that in individuals diagnosed with autism, high doses of vitamin B6 given with magnesium have been found to be extremely beneficial (Nye and Brice (2005)).

The present invention is a dietary supplement in the form of a syrup that is given to the child once or twice a day at a dose of about 1 to about 3 teaspoon(s) (about 5 to about 15 ml), based on the child's age. The syrup can be mixed with a beverage if needed. The same objective may be reached with a chewable tablet, capsule, gel cap, lollipop, lozenge, powder or effervescent tablet that contains the same formulation as the liquid formulation.

The present formulation may also be beneficial in treating and alleviating the symptoms of other neurological disorders, where a relationship exists between improper intestinal functioning and (brain) neuropathy.

OTHER REFERENCES

1. Aksoy, A., Duran, N. and Koksal, F. (2006) In vitro and in vivo antimicrobial effects of mastic chewing gum against *Streptococcus mutans* and *mutans streptococci*. *Arch. Oral Biol.* 51:476-81.
2. Clayton, P. T. (2006) B6-responsive disorders: a model of vitamin dependency. *J. Inherit. Metab. Dis.* 29:317-26.
3. Demestre, M., Messerli, S., Shahhossini, M., Kluwe, L., Mautner, V. and Maruta, H. (2007) Signal Therapy of NF (Neurofibromatosis) by Natural PAK1 Blockers. NF Conference, Abstract.

4. Hayashi, M. L., Rao, B. S., Seo, J. S., Choi, H. S., Dolan, B. M., Choi, S. Y., Chattarji, S. and Tonegawa, S. (2007) Inhibition of p21-activated kinase reescues symptoms of fragile X syndrome in mice. *Proc. Natl. Acad. Sci. USA.* 104:11489-94.
5. Huwez, F. U., Thirlwell, D., Cockayne, A. and Ala'Aldeen, D. A. (1998) Mastic gum kills *Helicobacter pylori*. *N Engl. J. Med.* 339:1946.
6. Jyonouchi, H., Geng, L., Ruby, A. and Zimmerman-Bier, B. (2005) Dysregulated innate immune responses in young children with autism spectrum disorders: their relationship to gastrointestinal symptoms and dietary intervention. *Neuropsychobiol.* 51:77-85.
7. Nye, C. and Brice, A. (2005) Combined vitamin B6-magnesium treatment in autism spectrum disorder. *Cochrane Database Syst. Rev.* 4: CD003497.
8. Parracho, H. M., Bingham, M. O., Gibson, G. R., and McCartney, A. L. (2005) Differences between the gut microflora of children with autistic spectrum disorders and that of healthy children. *J. Med. Microbiol.* 54:987-91.
9. White, J. F. (2003) Intestinal pathophysiology in autism. *Exp. Biol. Med.* 228:639-49.

The invention claimed is:

1. A formulation for treating symptoms of autism comprising effective amounts of:
   water-soluble a extract of mastic gum;
   L-Theanine;
   Passionflower a extract;
   Feverfew a extract; and
   Vitamin B6.

2. The formulation of claim 1 wherein a concentration of said water-soluble extract of mastic gum is between 5 to 100 mg/ml.

3. The formulation of claim 1 wherein a concentration of said L-Theanine is between 1 to 10 mg/ml.

4. The formulation of claim 1 wherein a concentration of said Passionflower extract is between 5 to 100 microgram/ml.

5. The formulation of claim 1 wherein a concentration of said Feverfew extract between 5 to 100 microgram/ml.

6. The formulation of claim 1 wherein a concentration of said vitamin B6 is between about 200 microgram/ml to about 10 mg/ml.

7. The formulation of claim 1 wherein a concentration of said water-soluble extract of mastic gum is between 5 to 100 mg/ml, and a concentration of said L-Theanine is about 1 to 10 mg/ml.

8. The formulation of claim 1 wherein a concentration of said water-soluble extract of mastic gum is between 5 to 100 mg/ml, a concentration of said L-Theanine is about 1 to 10 mg/ml, a concentration of said Passionflower extract is between 5 to 100 microgram/ml, a concentration of said Feverfew extract between 5 to 100 microgram/ml, and a concentration of said vitamin B6 is between about 200 microgram/ml to about 10 mg/ml.

9. The formulation of claim 1 wherein said formulation consists essentially of:
   said water-soluble extract of mastic gum;
   said L-Theanine;
   said Passionflower extract;
   said Feverfew extract; and
   said Vitamin B6.

10. The formulation of claim 1 wherein said formulation consists essentially of:
    said water-soluble extract of mastic gum;
    said L-Theanine;
    said Passionflower extract;
    said Feverfew extract; and
    said Vitamin B6; and
    wherein a concentration of a said water-soluble extract of mastic gum is between 5 to 100 mg/ml, a concentration of said L-Theanine is about 1 to 10 mg/ml, a concentration of said Passionflower extract is between 5 to 100 microgram/ml, a concentration of said Feverfew extract between 5 to 100 microgram/ml, and a concentration of said vitamin B6 is between about 200 microgram/ml to about 10 mg/ml.

11. The formulation of claim 1 wherein said formulation is in a dosage form selected from the group consisting of: a drink, a drink comprised of water, a syrup, a tablet, a gelcap, a capsule, a lozenge, a lollipop, a powder, and an effervescent tablet.

12. A method of treating a subject having at least some of the behavioral symptoms of autism spectrum disorders, comprising orally administering an effective amount of the formulation according to claim 1 to said subject.

* * * * *

UNITED STATES PATENT AND TRADEMARK OFFICE
CERTIFICATE OF CORRECTION

PATENT NO. : 8,652,545 B2  Page 1 of 1
APPLICATION NO. : 12/370577
DATED : February 18, 2014
INVENTOR(S) : Bart Nieuwenhuijsen It is certified that error appears in the above-identified patent and that said Letters Patent is hereby corrected as shown below:

In the Claims

Col. 3, line 27, Claim 1, line 3, add -- a -- before "water-soluble";

Col. 3, line 27, Claim 1, line 3, delete "a" between "water-soluble" and "extract of mastic gum";

Col. 3, line 29, Claim 1, line 5, add -- a -- before "Passionflower";

Col. 3, line 29, Claim 1, line 5, delete "a" between "Passionflower" and "extract";

Col. 3, line 30, Claim 1, line 6, add -- a -- before "Feverfew";

Col. 3, line 30, Claim 1, line 6, delete "a" between "Feverfew" and "extract";

Col. 3, line 40, Claim 5, line 2, add -- is -- between "said Feverfew extract" and "between 5 to 100"; and Col. 4, line 30, Claim 10, line 12, add -- is -- between "said Feverfew extract" and "between 5 to 100".

Signed and Sealed this
Second Day of September, 2014

Michelle K. Lee
*Deputy Director of the United States Patent and Trademark Office*